US005886155A

United States Patent [19]
Armah et al.

[11] Patent Number: 5,886,155
[45] Date of Patent: Mar. 23, 1999

[54] PURIFICATION OF MIRACULIN GLYCOPROTEIN USING TANDEM HYDROPHOBIC INTERACTION CHROMATOGRAPHY

[75] Inventors: George Enyimah Armah; Daniel Gyingiri Achel, both of Legon; Robert Asare Acquaah, deceased, late of Legon, all of Ghana, by Elizabeth Acquaah, executor; Makonnen Belew, Uppsala, Sweden

[73] Assignees: BioResources International Inc., Somerset, N.J.; Pharmacia Biotech AB, Uppsala, Sweden

[21] Appl. No.: 878,068

[22] Filed: Jun. 18, 1997

[51] Int. Cl.$^6$ .................................. C07K 1/00; A23J 1/00
[52] U.S. Cl. .................... 530/395; 530/370; 530/379; 530/402; 530/412; 530/416; 530/417; 530/418; 530/422; 530/427
[58] Field of Search ..................................... 530/395, 370, 530/379, 402, 412, 416, 417, 418, 422, 427

[56] References Cited

U.S. PATENT DOCUMENTS 3,676,149  7/1972  Fennel et al. ............................ 530/395
3,925,547  12/1975  Henkin et al. .......................... 530/395

FOREIGN PATENT DOCUMENTS 01-12462 B   3/1989   Japan .
01-12462B    3/1989   Japan .
WO93/10676   6/1993   WIPO .

OTHER PUBLICATIONS

"HiLoad™ Phenyl Sepharose® High Performance," Data File, Pharmacia Biotech. (18–1022–55).
Takahashi et al, *The Journal of Biological Chemistry*, vol. 265, No. 14, pp. 7793–7798, May, 15, 1990.
"Media For Hydrophobic Interaction Chromatography," Data File, Pharmacia Biotech.
"HiTrap® HIC Test Kit," Data File, Pharmacia Biotech.
"HiLoad™ Phenyl Sepharose® High Performance," Data File, Pharmacia Biotech (18–1022.55).
"Resource® ETH, Resource® ISO, Resource® PHE," Data File, Pharmacia Biotech.
"Phenyl Sepharose® 6 Fast Flow (low sub) Phenyl Sepharose 6 Fast Flow (high sub)," Data File 2040, Pharmacia Biotech, 1991.

Kurihara, "Taste–Modifying Protein from Miracle Fruit," Science, vol. 161, 1968, pp. 1241–1243.
Brouwer et al., "Miraculin, the Sweetness–inducing Protein from Miracle Fruit," Nature, vol. 220, Oct. 1968, pp. 373–374.
E. L. Giroux et al., "Purification and Some Properties of Miraculin, a Glycoprotein from *Sunsepalum dulcificum* Which Provokes Sweetness and Blocks Sourness," J. Agr. Food Chem., vol. 22, No. 4, 1974, pp. 596–600.
F.R. Dastoli et al., "Miracle–Fruit Concentrate," *Sweeteners*, Ch. 18, pp. 205–210.
N. Pintauro, "Miraculin, Glycyrrhizin and Artichoke Sweeteners," *Sweeteners and Enhancers*, Food Technology Review 190 40, Noyes Data Corp. 1977.
S. Theerasilp et al., "Complete Purification and Characterization of the Taste–modifying Protein, Miraculin, from Miracle Fruit," J. Biol. Chem., vol. 263, No. 23, pp. 11536–11539, Aug. 1988.
Y. Kurihara et al., "Isolation and Chemical Properties of Multiple Active Principles From Miracle Fruit," Biochimica et Biophysica Acta. 719, pp. 444–449, Elsevier Biomedical Press, 1982.

*Primary Examiner*—Cecilia J. Tsang
*Assistant Examiner*—Abdel A. Mohamed
*Attorney, Agent, or Firm*—Venable; Michael A. Gollin

[57] ABSTRACT

A method for purifying a plant protein comprises: (a) preparing a crude plant extract; (b) passing the crude plant extract with a first buffer solution through a guard column comprising a hydrophobic interaction chromatography medium of hydrophobicity sufficiently high to prevent tannins and polyphenols from eluting from the column in the presence of the buffer solution, but sufficiently low that a protein fraction elutes with the first buffer solution; (c) passing the protein fraction through a capture column coupled in series to the guard column, the capture column comprising a hydrophobic interaction chromatography medium of hydrophobicity sufficiently high to prevent the protein from eluting in the presence of the buffer solution; and (d) eluting the protein from the capture column as a purified fraction. Preferably the plant is miracle fruit, the protein is Miraculin, and the method comprises ion exchange chromatography and gel filtration chromatography of the purified fraction of the protein. Foods and beverages may be sweetened with the purified Miraculin.

24 Claims, 4 Drawing Sheets

Figure 1

MIRACULIN EXTRACT

```
         ┌──────────────┐      ┌──────────────┐
         │    GUARD     │      │   CAPTURE    │     TANDEM
         │   COLUMN     │      │   COLUMN     │      HIC
         │              │      │              │    COLUMNS
         │    Butyl     │      │   Phenyl     │
         │   Sepharose  │      │  Sepharose   │
         └──────────────┘      └──────────────┘
```

Fraction 1C ← | | → Fraction 1A
Fraction 1B ↓

```
         ┌──────────────┐
         │     ION      │
         │   EXCHANGE   │
         │    COLUMN    │
         │              │
         │      SP      │
         │ Sepharose FF │
         └──────────────┘
```

→ Fraction 2A+2C
Fraction 2B ↓

```
         ┌──────────────┐
         │     GEL      │
         │  FILTRATION  │
         │              │
         │   Sephacryl  │
         │   S-100 HR   │
         └──────────────┘
```

→ Fraction 3A
Fraction 3B ↓

PURIFIED MIRACULIN

PURIFICATION OF MIRACULIN GLYCOPROTEIN USING TANDEM HYDROPHOBIC INTERACTION CHROMATOGRAPHY

BACKGROUND OF THE INVENTION

This invention relates to plant protein purification. Specifically, the invention achieves the efficient separation of the functionally active plant glycoprotein, Miraculin, from the matrix of other constituents of vegetable matter in the berries of miracle fruits, using tandem hydrophobic interaction chromatography.

The taste-modifying properties of miracle fruits have been known to local people in West Africa for centuries, where the fruits have been used to sweeten sour foods and beverages such as koko and kenkey made from fermented maize and millet, and palm wine. The amazing properties of these fruits were first described in the scientific literature by F. W. Daniel (1) in 1852 who called it the 'miraculous berry of West Africa'. The active ingredient in the berries which is responsible for this effect was isolated and identified as a glycoprotein and subsequently named Miraculin by Kurihara and Beidler(2). These researchers extracted the pulp of the berries in sodium carbonate buffer at high pH and subsequently purified the extract by ion-exchange chromatography using DEAE Sephadex A-25 and CM Sephadex C-25 columns. Almost simultaneously, Brouwer et al. (3) also reported an alternate method of isolation of the active ingredient based on extracting the pulp of the berries into solutions of highly basic compounds such as salmine and spermine, followed by ammonium sulfate fractionation and gel filtration chromatography.

These early investigators noted the peculiar difficulties in isolating Miraculin from the berries. According to them, the active ingredient was highly labile and subject to rapid degradation by proteolytic enzymes present in the berries. Secondly, like many plant proteinaceous materials, Miraculin is found together with other components in plant tissues with which it very closely associated particularly polyphenolic coloring agents such that it is extremely difficult to isolate the free glycoprotein. In order to solve the latter problem, Giroux and Henkin (4) proposed grinding the pulp of the berries with insoluble polyvinylpyrollidone (PVP) in order to adsorb the polyphenolic compounds before extraction into sodium carbonate buffer.

A more recent purification protocol for isolating Miraculin was developed by Theerasilp and Kurihara (5) based on extraction of the pulp with 0.5M sodium chloride solution, followed by ammonium sulfate fractionation. Further purification was accomplished by ion-exchange chromatography on CM-Sephadex column and affinity chromatography using concanavalin A-sepharose column. The initial extraction with sodium chloride at neutral pH in lieu of alkaline (high) pH extraction was intended to minimize loss of the active ingredient which is believed to be sensitive to high pH.

A further improvement to this method was proposed by Kamimura et al (6) to include the addition of various acidic buffer media to the extraction solution in order to protect and stabilize Miraculin during isolation. The recommended media include aqueous acidic buffers such as sodium acetate, sodium citrate, sodium phosphate, glycine-HCl, and sodium borate.

In summary, prior approaches suffer from the peculiar problems associated with isolation of Miraculin from the berries. For example, tannins and other polyphenolic compounds which are co-extracted with Miraculin interfere with its isolation. Miraculin is also subject to rapid degradation by proteolytic enzymes present in the berries. Prior methods require use of large quantities of ammonium sulfate for fractionation which has adverse environmental impact during waste disposal. Existing methods require cold room operations during the purification process, which increases the cost of process-scale operations.

The methods developed so far for purifying Miraculin have been limited to laboratory scale operations suitable for obtaining research quantities (milligrams to grams range) of the active ingredient. In order to produce commercial quantities of Miraculin, a robust process is required which can be readily scaled-up to industrial scale. Such a method should also incorporate modem cost-effective protein purification technologies which can be operated in tropical environments where the berries are cultivated and harvested. Advantageously such a method should also be applicable to purification of other plant proteinaceous material.

REFERENCES

1. Daniel F. W. 1852. On *Synepalum dulcificum*, DeCand; or miraculous berry of Western Africa. Pharm J. 11, p 445.
2. Kurihara K., and Beidler L. M. 1968. Taste-Modifying Protein from Miracle Fruit. Science 161, pp 1241–1243.
3. Brouwer J. N., van der Wel H., Francke A., and Henning G. J. 1968. Miraculin, the Sweetness-inducing Protein from Miracle Fruit. Nature 220, pp 373–374.
4. Giroux E. L., and Henkin R. L. 1974. Purification and Some Properties of Miraculin, a Glycoprotein from *Synsepalum dulcificum* Which Provokes Sweetness and Blocks Sourness. J. Agr. Food Chem 22 (4), pp 595–601.
5. Theerasilp S., and Kurihara Y. 1988. Complete Purification and Characterization of the Taste-modifying Protein, Miraculin, from Miracle Fruit.J. Biol. Chem. 263 (23), pp 11536–11539.
6. Kamimura N., Makino T., Hirano A., Kurihara Y., and Hagino T. 1993.Process for Producing Sweetness Inducer Miraculin, PCT/WO 93/10676.

SUMMARY OF THE INVENTION

This invention relates to the use of tandem hydrophobic interaction chromatography (HIC) to facilitate the initial isolation of a plant protein, such as the taste-modifying glycoprotein, Miraculin, from extracts of the pulp of miracle fruits. The initial purification is accomplished by two (tandem) HIC columns coupled in series such that the first column acts primarily as a guard column to remove most of the polyphenols (defined to include pigments, tannins and other polyphenolic compounds) in plant tissue extracts which are co-extracted with Miraculin. As a result Miraculin becomes free of plant pigments and is efficiently bound to, or captured on the second HIC column. The partially purified Miraculin obtained after the HIC step is further purified to homogeneity preferably by ion-exchange and followed by gel filtration chromatography. Such a separation is therefore based on hydrophobicity, charge, and molecular size.

Tandem HIC eliminates the need for ammonium sulfate fractionation of crude Miraculin extracts, as commonly practiced in the prior art while achieving a purity equivalent to or better than prior art methods. Ammonium sulfate fractionation involves tedious processing conditions using as much as 50–80% saturated (2–3M) concentrations of ammonium sulfate which leads to yield losses of the saturated active ingredient. The latter procedure also involves cumbersome operations such as repeated precipitation and centrifugation steps which are expensive to scale-up. In contrast, the inventive method requires pretreatment of the extract with considerably lower concentrations (as low as 10% or less) of ammonium sulfate before the HIC step. Moreover, the sample can be applied to the column as soon as it is extracted thus minimizing proteolytic degradation processes.

The inventive method succeeds where previous efforts have been inadequate. It is robust and fast enough that the entire purification process can be performed at room temperature without loss of activity of Miraculin. This represents a significant advantage over prior art methods which requires operations in refrigerated cold rooms to prevent loss of Miraculin activity during processing. Operating at ambient temperatures provides significant advantages and savings in investment and operating costs for commercial processing of Miraculin in tropical environments where the berries grow.

According to the invention, HIC may be used as the first step in the purification of a crude extract of Miraculin. This approach was not previously known or suggested for isolating plant proteins such as Miraculin. In a tandem HIC setup according to the invention, two columns packed with different kinds of hydrophobic adsorbents are connected in series. The first column is packed with a relatively weak hydrophobic adsorbent having hydrophobicity sufficiently high to bind tannins and other polyphenolic compounds and plant pigments but low enough that the glycoprotein elutes with the equilibration buffer. The second column is packed with a more hydrophobic adsorbent that has a hydrophobicity sufficiently high to bind the glycoprotein in the same equilibration buffer. Both columns are equilibrated with the same starting buffer and are linked together during the adsorption step. The tandem arrangement of HIC columns is advantageous because the first column binds the most hydrophobic solutes in the crude extract (i.e. plant pigments, protein impurities, etc.) while the second column effectively binds Miraculin together with some other protein impurities and faintly colored substances. The two columns may then be disconnected so that Miraculin can be separately eluted from the second column using low ionic strength buffers. This method has the following advantages which could not have been appreciated previously:

i) Two chromatographic operations are reduced to a single step thus significantly reducing the processing time.

ii) Sample preparation is reduced to a minimum since precipitation of the extract with large amounts of ammonium sulfate and subsequent centrifugation steps are avoided.

iii) The partially purified Miraculin is eluted with a buffer of low ionic strength so that it can be applied to a cation exchanger (the subsequent step in the purification procedure) after a simple two-fold dilution eliminating the need for dialysis, which is common in other published procedures. This is extremely convenient since it reduces significantly operational costs especially on a commercial scale.

iv) The duration of the entire purification process is significantly shortened such that proteolytic degradation of Miraculin is reduced to a minimum, even when the chromatography is performed at room temperature. This obviates the need for installation of very costly cold room facilities (as required in previously published methods) in a tropical environment where the berries are grown since they need to be processed immediately after harvesting.

v) The guard column can be regenerated, and the tandem HIC column system can be reused repeatedly.

vi) The cumulative advantages of simplicity, convenience, and speed of operations provided by this protocol result in higher throughput and increases in productivity and yield of the overall purification process.

The tandem packed column purification method is preferred. However, the HIC purification step can also be performed in a batch-wise mode where the adsorbents need not be packed in a column. This is especially applicable for the medium used in the guard HIC column, where for instance the crude extract of Miraculin can be mixed with the adsorbent in a stirred tank for an hour or two to remove the hydrophobic plant pigments. The supernatant can then be applied to a packed column of the capture medium. There may be some advantages to this mode of operation, however in general the tandem column arrangement is more simple, convenient and efficient particularly for cleaning and regeneration of the gels for re-use.

Further objectives and advantages will become apparent from a consideration of the description, drawings, and examples.

BRIEF DESCRIPTION OF THE DRAWINGS

The invention is better understood by reading the following detailed description with reference to the accompanying figures, in which like reference numerals refer to like elements throughout, and in which:

FIG. 1 is a flow chart of the purification process for Miraculin.

DETAILED DESCRIPTION OF THE PREFERRED EMBODIMENTS

Figure 2:
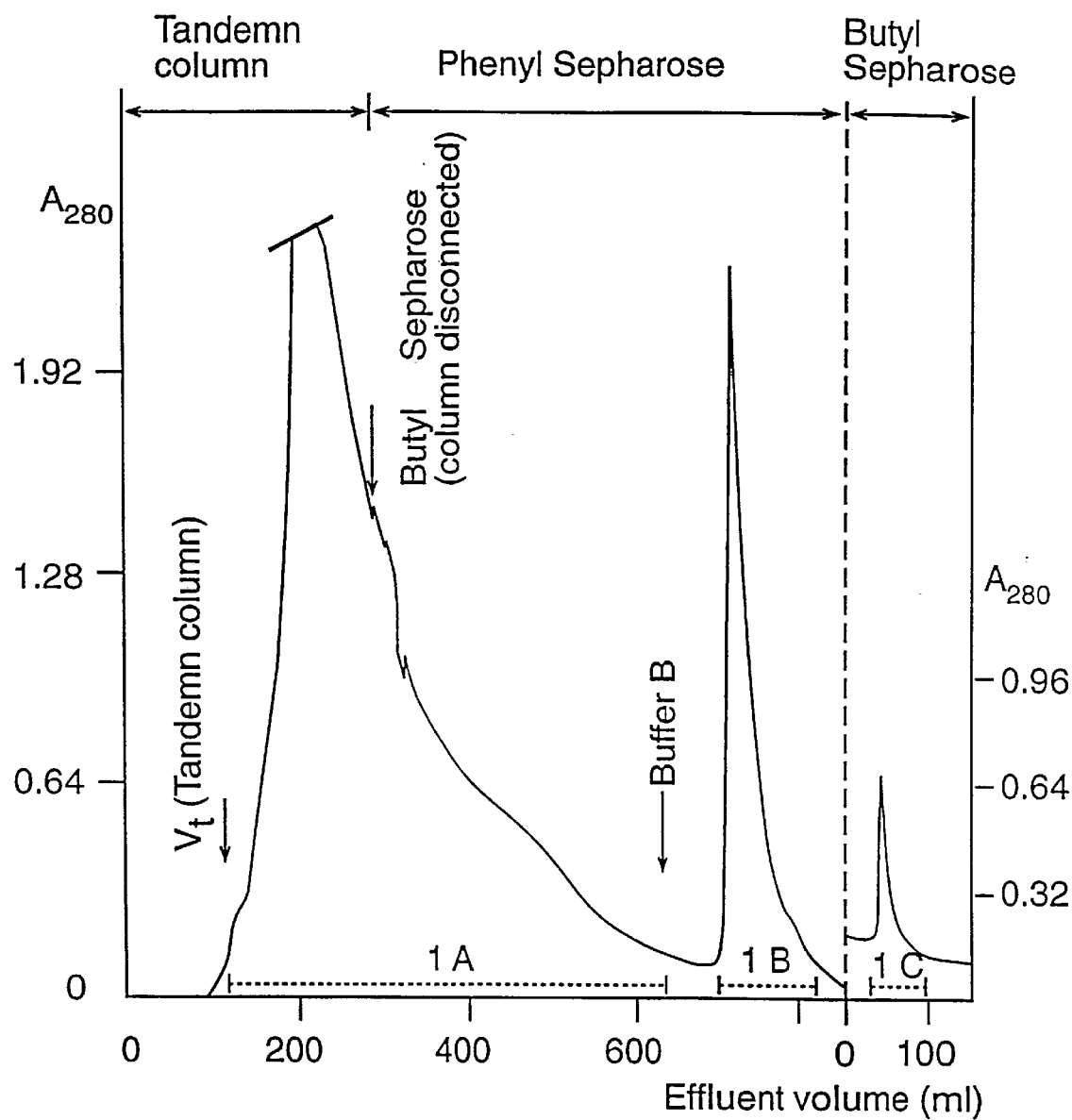
FIG. 2 shows the ultraviolet (UV) absorption profile of the eluted fractions collected from tandem HIC columns.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

A method for purifying plant proteinaceous material comprises: (a) preparing a crude plant extract; (b) passing the crude plant extract with a first buffer solution through a guard column comprising a hydrophobic interaction chromatography medium of hydrophobicity sufficiently high to absorb tannins and polyphenols to prevent them from eluting from the column in the presence of the buffer solution, but sufficiently low that a proteinaceous fraction elutes with the first buffer solution; (c) passing the proteinaceous fraction through a capture column coupled in series to the guard column, the capture column comprising a hydrophobic interaction chromatography medium of hydrophobicity sufficiently high to prevent the glycoprotein from eluting in the presence of the buffer solution; and (d) eluting the proteinaceous material from the capture column as a purified fraction. Preferably the proteinaceous material is a protein, peptide, or glycoprotein, most preferably Miraculin.

The method may further comprise uncoupling the guard column and the capture column before eluting the glycoprotein, and may further comprise regenerating the guard column by eluting the bound fraction with a regenerating buffer or reagent, preferably sodium hydroxide in a concentration of from about 0.5 to about 1M.

The hydrophobic interaction chromatography medium is preferably a polymeric or cellulosic medium like cross-linked agarose beads (e.g. Sepharose gels). Preferably the hydrophobic interaction chromatography medium with low hydrophobicity has covalently linked alkyl, preferably $C_2$ to $C_6$ (or $C_8$ up to $C_{10}$) functional groups, most preferably a butyl functional group; and the high hydrophobicity hydrophobic interaction medium has covalently linked cyclic, polycyclic, or heterocyclic aromatic functional groups, preferably a phenyl group.

In HIC, substances are separated on the basis of their varying hydrophobic interactions with an uncharged chromatography material containing hydrophobic groups. Such separation is suitable for proteins because most include amino acid constituents having hydrophobic side chains which may be exposed under the chromatographic conditions to allow binding to the chromatography material. High hydrophobicity may also be attained by increasing the degree of substitution or density of ligands (akyl or aryl) on the support. The preferred commercially available media are low sub (substituted), but there are also highly substituted alkyl resins which have high hydrophobicity and may be suitable as material for column I or II in tandem HIC according to the invention.

Hydrophobic interaction is favored under conditions of high ionic strength, and elution may be achieved with an elution buffer with reduced salt concentration. In principle, the HIC separation technique is based on the phenomenon of inducing conformational changes in proteins in the presence of low to moderate salt concentrations exposing hydrophobic regions which enable protein adsorption to hydrophobic chromatographic supports. The adsorbed proteins are eluted by decreasing salt concentrations which reverse the environment leading to loss of hydrophobic interactions between the proteins and the support. The type of salt, detergents, temperature, pH and other factors may be controlled to optimize the separation. For example, the following salts may be used: ammonium sulfate, sodium sulfate, sodium citrate, sodium chloride, ammonium thiocyanate, and potassium, magnesium, and calcium salts thereof, and combinations. The size of the media and the resulting flow rate also affect separation results, and a suitably large exclusion size is desirable.

Suitable hydrophobic interaction chromatography media may be any currently available or later developed materials having the characteristics necessary to practice the claimed method. Preferred HIC media are Sepharose-based HIC media supplied by Pharmacia Biotech, Uppsala, Sweden. Sepharose products were used in preference because of the ease of their regeneration and reliable operation for industrial-scale operations. However, the inventive method is applicable to other HIC media based on synthetic, organic, or natural polymers such as cellulose, silica, polyacrylamide, polymethacrylate, dextran, etc., containing alkyl, aryl, or ether ligands with suitable hydrophobicity to selectively bind and then elute the polyphenols from the guard column and the target protein from the capture column.

A preferred type of media is Sepharose beads into which alkyl or aryl groups have been introduced by reacting the monosaccharide units to the hydrophobic ligand via the corresponding glycidyl ether, providing stable ether bonds. Cross-linked Sepharose such as CL-4B is preferred. Appropriate characteristics include average bead sizes of 30 to 100 microns, ligand densities of 5 to 50 micromoles per ml gel, and beads containing 4–6% agarose. Ligands with alkyl chain lengths between 2 and 10 carbons are available as are a corresponding series of alkylamines, with increasing hydrophobicity as the chain length increases. Phenyl Sepharose is between butyl and pentyl variants in hydrophobicity, and also binds to aromatic rings in contaminants and target proteins via $\pi$—$\pi$ interactions. Other hydrophobic ligands have amino or carboxyl groups, such as AH-Sepharose 4B and CH-Sepharose 4B, which have ionizable groups at the end of 6-carbon spacer arms, and combine hydrophobic and ion exchange effects. Preferred Sepharose HIC media are non-ionic fast flow variants to facilitate shorter processing times. Other types of media include polystyrene/divinyl benzene matrix particles coupled to ether, isopropyl, or phenyl ligands.

The practitioner will understand how to select an appropriate capture column and compatible equilibration buffer that will capture the target protein or HIC medium peptide, and then to select a less hydrophobic HIC media for the guard column that will bond polyphenolic and pigment contaminants in the same equilibration buffer, while allowing the target protein to pass through to the capture column.

The method may further comprise ion exchange chromatography and gel filtration chromatography of the glycoprotein partially purified by the tandem HIC step. Other separatory techniques may be employed instead of or in addition to these chromatography steps.

The crude plant extract may be pre-conditioned with a low-salt medium having a salt concentration of less than about 10%, and the operations may be carried out at room temperature. The product of the process of the invention may be quite pure, preferably at least about 95%. With Miraculin, the purified product may comprise multiple variants, such as truncated variants lacking one or more amino acid residues at the N-terminal or C-terminal ends, or glycoforms having different glycosylation patterns.

In a preferred embodiment, the invention encompasses a three step purification procedure for Miraculin from a dark-brown crude extract. The adopted procedure is reproducible, can be scaled up as required, takes no more than about two days to accomplish, and leads to a homogeneous product which is at least 95% pure as judged by SDS-PAGE electrophoresis and re-chromatography on IEC and gel filtration columns. The procedure is also well adapted for preparing a partially purified (bulk or food-grade) or a highly purified (analytical grade for research purposes) Miraculin, depending on its intended use. As regards the preparation of the food-grade Miraculin, a single purification step (HIC) may be sufficient to obtain a concentrated, purified and potent product which is economically competitive compared with existing processes.

The invention preferably involves an application of hydrophobic interaction chromatography (HIC) to address the problems faced in Miraculin isolation. In principle, the HIC separation technique is based on the phenomenon of protein adsorption on hydrophobic supports in the presence of low concentrations of salt. Hydrophobic resins may be based on alkyl and aryl groups such as butyl and phenyl functional groups covalently attached to a chromatographic medium such as a polymer like cross-linked agarose beads (e.g. Sepharose gels). Before adsorption to the column, the crude plant extract is preferably pre-conditioned in a low salt medium. The adsorbed proteins are eluted by decreasing concentrations of the salt in the buffer, preferably a stepwise decrease, which results in selective desorption from the column.

The advantages of the inventive method include the fact that it is robust, requires minimum sample pre-treatment, can be done at a fast rate, does not require cooling, and removes the most hydrophobic contaminants such as tannins and other polyphenolic compounds which would interfere with isolation of a target protein by subsequent separations based on charge, molecular size or other chromatographic criteria. The highly hydrophobic nature of the polyphenolic compounds which interfere with plant protein isolation makes tandem HIC a highly attractive method to remove these compounds at the initial steps of the purification of the protein, particularly with Miraculin.

The use of HIC columns in tandem provides the unique advantage that the "weaker" adsorbent (e.g. Butyl-Sepharose 6 FF) effectively binds the most hydrophobic plant pigments without binding the target protein, e.g. Miraculin. In this regard it is possible that in addition to hydrophobic interactions the polyphenolic compounds also engage in π—π interactions with aromatic rings of the phenyl HIC medium. The aggregate strength of these interactions makes it difficult to dislodge the plant pigments once bound to the phenyl HIC column, necessitating pretreatment of the extract with a guard column consisting of less interactive akyl groups. This saves the capture column (e.g. Phenyl Sepharose 6 FF) from being fouled or "destroyed" by the plant pigments, which could be bound to it so strongly that regeneration would be difficult, if not impossible. The use of tandemly coupled HIC columns has made it possible to use the capture column (e.g. Phenyl Sepharose 6 FF) repeatedly without any noticeable deterioration in its adsorption characteristics.

The adopted purification procedure is simple, reproducible, economical, and well-suited for process-scale operations. The inventive method has broad applicability to the isolation and purification of plant proteins and glycoproteins from plant and vegetable matter, particularly from those materials comprising tannins, pigments, and other polyphenol components that coextract and/or comigrate with the target protein. The method is especially advantageous for target proteins that are labile and susceptible to proteolysis.

A preferred embodiment of the invention is shown in FIG. 1. The first HIC column (I) consists of commercially available Butyl-Sepharose and the second column (II) consists of Phenyl-Sepharose supplied by Pharmacia Biotech AB. The two HIC columns are coupled in series because they are operated under the same chromatographic conditions such as the composition of buffers used for absorption or desorption, ammonium sulphate concentration, flow rate, etc. This arrangement reduces an otherwise two-step chromatographic process into a single step thus saving time and operational costs during the initial purification of Miraculin from the crude extract of miracle berries.

In general, the inventive method is applicable wherever the contaminant polyphenols, pigments, and tannins have a greater hydrophobicity than the target proteinaceous material as sample solutes in the equilibration buffer. The target proteinaceous material can be expected to have an induced hydrophobicity that is increased in the salt milieu of the buffer. The induced hydrophobicity of the target protein is then reduced in the elution buffer, which has a lower ionic strength, to elute the target proteinaceous material.

The relatively weaker hydrophobic medium, which is packed in the first (guard) column (I) strongly binds the most hydrophobic components (polyphenols and other dark plant pigments) in the crude extract of miracle berries without binding Miraculin itself. The second (capture) column (II) containing Phenyl Sepharose 6 FF (low sub) binds Miraculin together with some faintly colored plant pigments and some protein impurities. This arrangement serves two important functions:

i) it effectively purifies and concentrates Miraculin in a single step;

ii) it is relatively easy to regenerate the two adsorbents by mild and cheap solvents (e.g. 0.5–1M NaOH) which makes it possible to use these adsorbents for several cycles of reproducible operations. This initial purification step is convenient and cost-effective for either laboratory and/or industrial-scale operations.

By way of comparison, one alternative is to use column II alone for the initial purification and concentration of Miraculin. Although this is possible in principle, it was found to be unattractive in practice. This is because the dark pigments in the crude extract bind so strongly to this column that satisfactory re-generation of the adsorbent is costly since it requires the use of organic solvents like ethanol or iso-propanol. The useful life-time of the column is also reduced to a few cycles of operation. The use of column II alone thus would increase the investment and operational costs for the initial purification of Miraculin. The use of tandem HIC therefore brings unexpected benefits.

The inventive method is applicable to separation of other plant proteins, glycoproteins, and peptides from extracts of any vegetable matter including fruits, seeds, leaves, flowers, stem, bark, and roots.

The starting material may be mechanically separated and is prepared as a crude homogenate, preferably in an aqueous liquid, although alcohol or non-aqueous extracts are also feasible. Non-denaturing conditions are preferred. For a basic protein, an acid extraction is useful, and for an acidic protein such as Miraculin, an alkaline extraction may be preferred. Salts may be helpful in promoting extraction and in equilibrating the extract for application to the guard column.

After HIC, any suitable conventional technique known to practitioners may be used, such as ion exchange chromatography, gel filtration, affinity chromatography, and so on. For industrial applications the simpler purifications are preferred.

Material purified according to the invention may be used in alimentary products such as flavorants, foods, or beverages. The invention contemplates foods and beverages sweetened by HIC-purified Miraculin.

EXAMPLE 1

Depulping, Washing and Sonication

One hundred grams (100 g) of miracle fruit berries were depulped in a Laboratory Pulper (Food Processing Equipment Corp, FPECO, Kalamazoo, Mich.) using a screen size adapted to the seed size of the berries. The seeds and coat debris from the berries were discarded. The pulp was suspended in 300 ml of water and centrifuged at 5,000 rpm for 15 minutes. The supernatant was discarded and the wash step was repeated (thrice) with the pellet fraction. The supernatant at this stage was slightly colored and did not have taste-modifying activity. The pellet fraction (60 g) was then suspended in 300 ml of 0.5M NaCl solution. The suspension was sonicated for 30 minutes with an Ultrasonic Disintegrator (Soniprep, Fison Ltd.) to disrupt the plant cellular tissues and release the active ingredient. The extract was then centrifuged at 10,000 rpm for 20 minutes and the supernatant (310 ml), which was light brown in color with taste-modifying activity, was recovered.

Buffer Solutions:
A. 20 mM sodium phosphate buffer, containing 0.6M ammonium sulphate, pH 6.8 (conductivity=ca. 80 mS/cm at 20° C.)
B. 20 mM sodium phosphate buffer, pH 6.8 (conductivity=ca. 2 mS/cm at 20° C.)
C. 20 mM sodium phosphate buffer, containing 0.05M NaCl, pH 6.8 (conductivity=ca. 7 mS/cm at 20° C.)
D. 20 mM sodium phosphate buffer, containing 0.12M NaCl, pH 6.8 (conductivity=ca. 33 mS/cm at 20° C.)
E. 20 mM sodium phosphate buffer, 0.35M NaCl, pH 6.8

Hydrophobic Interaction Chromatography (HIC)

The tandem HIC system consisted of column I containing 50 ml Butyl-Sepharose (Butyl-S-Sepharose 6 FF, Pharmacia Biotech AB, or other butyl Sepharose giving similar results), which acts as the guard column connected in series with column II containing 100 ml Phenyl Sepharose (6 FF, low sub, Pharmacia Biotech AB), which acts as a capture column.

The separation media were each packed in XK26 columns to a bed height of 14.5 cm (Vt=77 ml) and 8.5 cm (Vt=45 ml), respectively. The tandem column system was washed with de-ionized water followed by pre-equilibration with Buffer A.

The crude clarified Miraculin extract was pre-conditioned as follows. The ionic strength of the extract was increased to raise its conductivity to that of the equilibration Buffer A by dissolving 25 g of ammonium sulfate to obtain a concentration of 0.6M $(NH_4)_2SO_4$. The pre-conditioned extract was loaded onto column I at a constant flow rate of 5 ml/min. Column I was found to strongly bind the brown plant pigments and other impurities in the extract. The effluent from column I then passed directly to column II which preferentially bound Miraculin as discussed below. After sample application, the tandem column was washed with sufficient volume of equilibration Buffer A (about 2.5 times the total bed volume) to elute the unbound impurities. Column I was then disconnected from column II and the bound Miraculin was eluted from column II using Buffer B.

Column II was then washed with a further 300 ml of Buffer A (ca. 4-times its bed volume) to further elute the unbound material. The bound fraction, which contained the Miraculin from the applied sample, was then eluted by washing the column with about 200 ml (ca. 3-bed volumes) of Buffer B.

The Butyl-Sepharose column (I) was then re-connected to the pump and washed with 100 ml (ca. 2-times its bed volume) of Buffer B to elute the less tightly bound materials on it. Each column was then washed with at least 3-bed volumes of 0.5–1M NaOH to remove the most tightly bound components of the sample (light to dark brown plant pigments) followed by washing with at least 3-bed volumes of de-ionized water. The plant pigments seemed to bind more strongly as their residence time in these two columns increases. The regenerated columns can then be equilibrated as described above prior to their subsequent re-use.

The chromatogram obtained from this step is shown in FIG. 2. Peak 1A is the unbound fraction on both columns which is light yellow in color and has no taste-modifying activity. This fraction was consequently discarded. Peak 1B is eluted from column II with Buffer B and contains Miraculin free from much of the plant pigments and other impurities. Peak 1C was obtained by eluting from column I after disconnection.

A summary of the results obtained is shown in Table 1.

TABLE 1

| Pool | Volume | $A_{280}$ | Total $A_{280}$ | % of applied |
|------|--------|-----------|-----------------|--------------|
| 1A   | 630    | 1.02      | 643             | 64.6         |
| 1B   | 142    | 0.73      | 104             | 10.4         |
| 1C   | 100    | 0.24      | 24              | 2.4          |

The unbound fraction (1 A) accounts for ca. 65% of the total $A_{280}$ applied to the column. This fraction does not contain Miraculin, as judged by SDS-PAGE of the concentrated and reduced sample. This chromatographic step is therefore very effective in removing most of the impurities found in the crude extract of the miracle berries.

Fraction 1B accounts for ca 10–12% of the total $A_{280}$ applied to the tandem column. This fraction contains Miraculin as judged by SDS-PAGE of the concentrated and reduced sample. The volume of the pooled fraction 1B is about 2-times that of the sample applied to the column indicating that the partially purified Miraculin is not excessively diluted.

Fraction 1C, which is eluted from the Butyl-Sepharose column, accounts for ca 3% of the total $A_{280}$ of the applied sample and does not contain Miraculin as judged by SDS-PAGE of the concentrated and reduced sample. The results thus show that ca. 20% of the applied $A_{280}$ was still bound to the columns after elution with Buffer B. Further washing of each column with 30% iso-propanol did not elute a significant amount of the bound material.

Prior to regeneration, about 80% of the guard (Butyl) column was dark brown in color while the capture (Phenyl) column was light yellow to the extent of ca. 70%. This discoloration is due to the plant pigments which were co-extracted with the Miraculin and are apparently very hydrophobic.

Ion Exchange Chromatography

Figure 3:
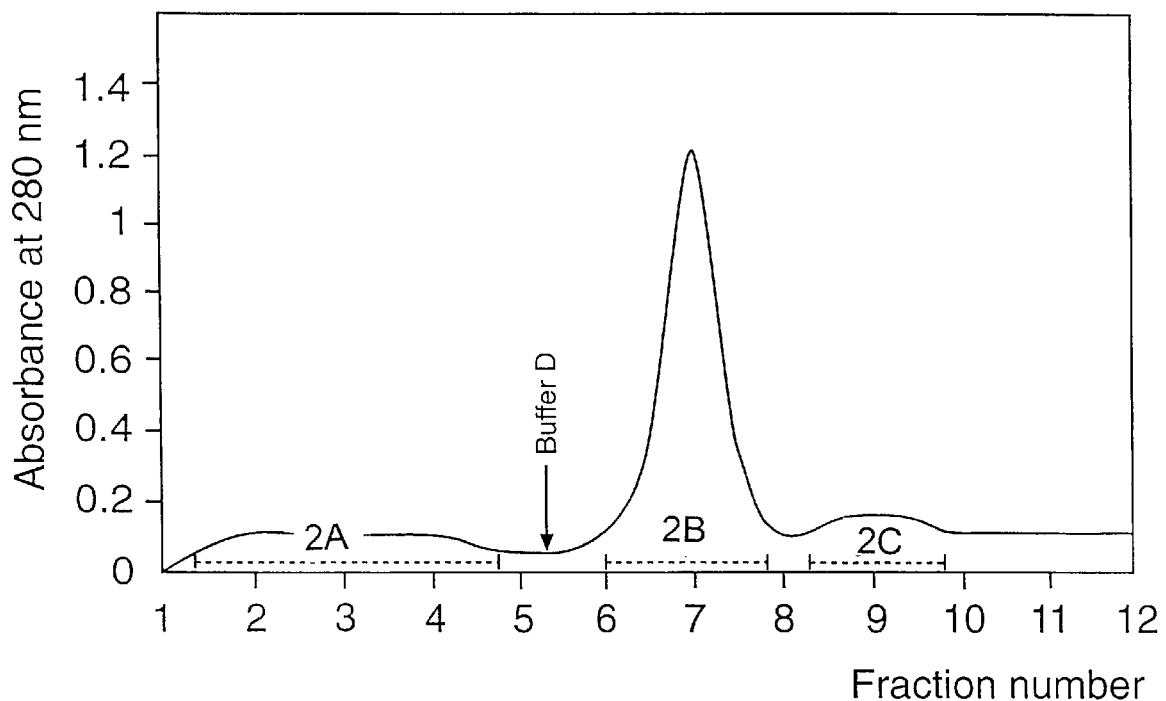
FIG. 3 shows the UV elution profile for ion exchange chromatography of pooled and concentrated fraction 1B from the HIC step.

Peak 1B from the previous step was pooled together and diluted with Buffer B to twice its volume and then loaded onto a 50 ml SP-Sepharose FF ion exchange column (Pharmacia Biotech, AB). Prior to loading, the column was pre-equilibrated with Buffer C. After loading, the ion exchange column was washed with Buffer D. The column was then eluted with Buffer E. The elution profile obtained is shown in FIG. 3. Peaks 2A and 2C showed no taste-modifying activity. Miraculin activity was found in the larger peak, Peak 2B, which was slightly colored.

The use of a step-elution process was preferred over a gradient because gradient mixing apparatus was not required, dilution of the eluted sample was minimized, and process time was decreased.

Gel Filtration

Figure 4:
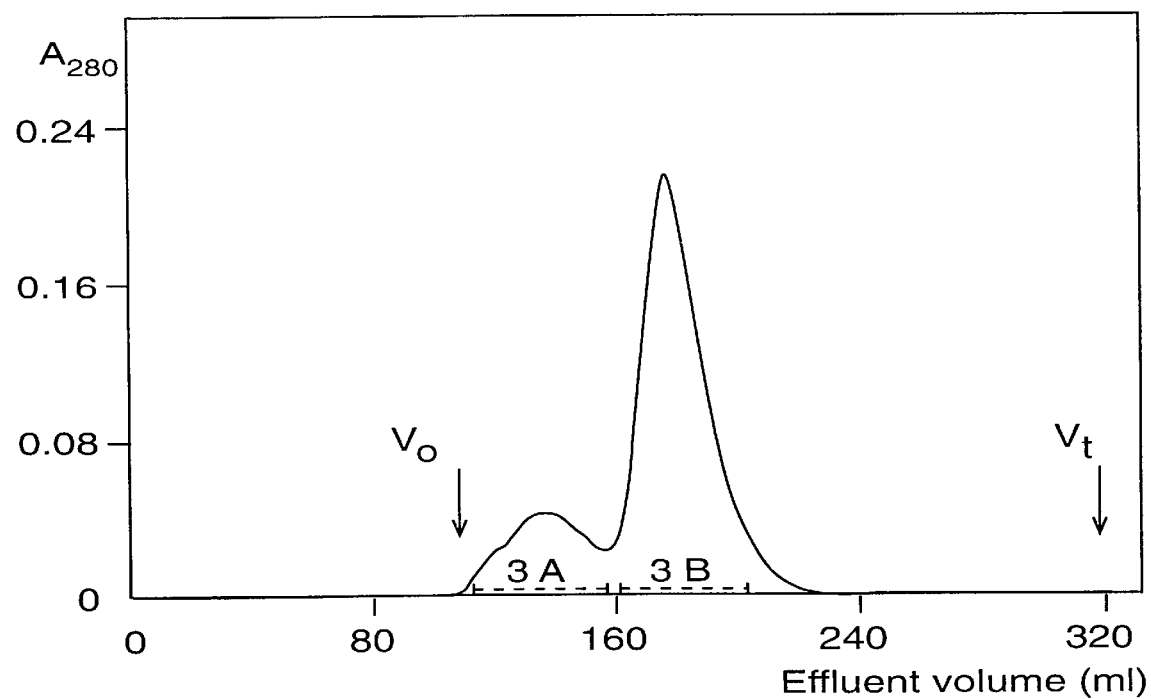
FIG. 4 shows the UV elution profile for gel filtration chromatography of fraction 2B from the ion exchange chromatography step.

Fraction 2B from the ion exchange step was pooled and concentrated using an Amicon concentrator with a 10 kDa molecular weight cut-off membrane. The concentrate (10 ml) was then loaded on a 300 ml column of Sephacryl S-100 (Pharmacia Biotech AB) equilibrated with Buffer D. (Sephacryl S-200 HR has also been used.) Fraction 3A contains the impurities found in the applied fraction 2C, as shown in FIG. 4. Elution of the column with Buffer E at a flow rate of 15 cm/h resulted in the elution profile shown in FIG. 4. Purified Miraculin with potent taste-modifying activity was eluted in the major peak, Peak 3B. This was pooled, dialyzed, lyophilized and stored at −20° C. until further use.

The recovery of $A_{280}$ absorbing material after this last step is apparently quantitative as shown in Table 2. The elution profile obtained here was found to be reproducible from run to run.

TABLE 2

| Pool | Volume (ml) | $A_{280}$ | Total $A_{280}$ | % of applied |
|---|---|---|---|---|
| 3A | 46 | 0.07 | 3.22 | 20.6 |
| 3B | 45 | 0.25 | 11.3 | 72 |

EXAMPLE 2

Characterization of Miraculin

SDS polyacrylamide gel electrophoresis (PAGE) of a sample from Peak 3B showed a single band with relative molecular weight of 25 kDa. This corresponds to the molecular weight of the monomeric form of Miraculin. The high purity of the Miraculin obtained is confirmed by the absence of secondary bands on the electrophoresis gel. SDS electrophoresis (under non-reducing conditions) also showed the presence of a single major band with a molecular weight of 43 kDa which corresponds to the naturally-occurring, dimeric form of Miraculin. Further analysis of the purified protein by sequencing from the amino-terminal end confirmed that the first ten amino acid residues correspond to the sequence reported in the literature for purified Miraculin.

The purity of Miraculin obtained according to the invention was as high as that of a prior art Miraculin prepared by a tedious procedure which is both time-consuming and difficult to scale-up. The purified Miraculin had a molecular weight of ca. 25 kDa or 43 kDa when determined by gradient SDS-PAGE under reducing or non-reducing conditions, respectively. According to published data, these values correspond to the monomeric (reduced) and dimeric (oxidized) forms of Miraculin. Its partial amino-terminal sequence (the first 10 residues) was found to be identical to the known sequence of this protein as found in an *Amino Acid Sequence Data Base*. Its biological activity, i.e., its taste-modifying effect, was also found to be typical for Miraculin as determined by an impartial panel using a double-blind biological assay procedure.

Miraculin is a basic glycoprotein (pI ca. 9.1) composed of 191 amino acid residues and with a carbohydrate content of 13.9%. The carbohydrates are linked to 2 asparagine residues situated near the amino- and carboxyl-terminal ends of the single chain molecule. It has a high content (12%) of the basic amino acids Lys and Arg which might suggest that it is vulnerable to proteolytic degradation. On the other hand, its high content of carbohydrate might protect it from such proteolytic attack and thus increase its stability. It also contains 7 Cys residues, six of which form 3 intra-molecular disulfide bonds leaving one Cys residue free. This suggests that the free Cys residues from two single-chain Miraculin molecules can form an intermolecular disulfide bridge resulting in a homo-dimer of this protein.

Variable molecular weights have been assigned to this protein depending upon the method used for such determinations. By SDS-PAGE of the reduced and denatured Miraculin, a molecular weight of 28 kDa was obtained. Using the same technique, the non-reduced and denatured Miraculin gave a molecular weight of 43 kDa. By low-angle laser light scattering technique, a molecular weight of 90 kDa was determined for the native Miraculin. From amino acid sequence data and its carbohydrate content, a molecular weight of 24.6 kDa was calculated. These results thus indicate that the purified and native Miraculin is a tetramer of the 25 kDa monomer while native Miraculin is a dimer in its crude state. Both the dimer and tetramer elicit the expected biological activity (i.e., taste-modifying effect) in the crude extract.

Purified Miraculin (fraction 3B) gave a single, symmetrical peak upon re-chromatography on the same Sephacryl S-200 column used above or upon ion-exchange chromatography on a Mono S HR 5/5 column at two different pH values and different gradient elution protocols. SDS-PAGE of the reduced or non-reduced purified protein gave essentially a single band with some minor bands. The migration positions of these "impurities" suggest that they may be monomeric or polymeric forms of Miraculin.

As verification, the elution position of purified Miraculin from a Sephacryl S-100 column was the same as that of α-chymotrypsinogen run on the same column under identical conditions. Its molecular mass is thus approximately 25 kDa which agrees well with that calculated from SDS-PAGE of the reduced protein or that reported by other workers (24.6 kDa, see ref. 1) for its monomeric form. On the other hand, SDS-PAGE of the non-reduced Miraculin gave a single dominant band with $M_r$ close to that of ovalbumin (43 kDa) and some faint bands corresponding to its monomeric and tetrameric forms. The native form of purified Miraculin is thus predominantly a homo-dimer, which is consistent with data showing that the single-chain protein contains 7 cysteine residues of which 6 form three intra-chain disulfide bridges leaving one cysteine residue free. This residue can easily form an inter-chain disulfide bridge with another molecule of Miraculin resulting in a homo-dimer. This conclusion also agrees well with the report by Kurihara (1992) and establishes the purity and identify of the Miraculin purified according to the invention.

Further evidence for the identity of the purified Miraculin was provided by partial amino-terminal sequencing of pooled fraction 3B according to the well established Edman degradation method using an Applied Biosystems Model 477 A sequencer. The phenylhydantoin (PTH) amino acid derivatives were identified using an Applied Biosystems Model 120A PTH analyzer. The results obtained are shown in Table 3.

TABLE 3

Partial amino-terminal sequence of residues 1–10 of purified Miraculin

Major form (ca. 70%):  1  5  10
$NH_2$.Asp—Ser—Ala—Pro—Asn—Pro—Val—Leu—Asp—Ile

Minor form (ca. 30%):  1  5  9
$NH_2$.Ser—Ala—Pro—Asn—Pro—Val—Leu—Asp—Ile

The results of the partial amino-terminal sequence of purified Miraculin (pool 3B, FIG. 4) showed that at least 70% corresponded to that of the published sequence for Miraculin (Kurihara, 1992). A "minor form" of the purified protein (less than 30%) had a sequence which is identical to the "major form" with the exception that it lacked the $NH_2$-terminal Asp residue.

The results obtained might also suggest that the "minor form" is a proteolytically modified variant of the "major form" of purified Miraculin. There is, however, no evidence for a proteolytic cleavage of the purified Miraculin at sites other than the $NH_2$-terminal residue. This is because the sequence of the "minor form" could not be localized anywhere in the molecule. It is also possible that the heterogeneity on the $NH_2$-terminal end of the molecule might be due to a natural variant of the same Miraculin protein that is present in the purified sample.

The embodiments illustrated and discussed in this specification are intended only to teach those skilled in the art the best way known to the inventors to make and use the invention. Nothing in this specification should be considered as limiting the scope of the present invention. Modifications and variations of the above-described embodiments of the invention are possible without departing from the invention, as appreciated by those skilled in the art in light of the above teachings. It is therefore to be understood that, within the scope of the claims and their equivalents, the invention may be practiced otherwise than as specifically described.

What is claimed is:

1. A method for purifying Miraculin comprising:
   (a) preparing a miracle fruit extract;
   (b) combining the extract in the presence of an equilibration buffer with a hydrophobic interaction chromatography medium of hydrophobicity sufficiently high to bind polyphenols in the presence of the buffer solution, but sufficiently low that Miraculin is unbound and remains in the buffer;
   (c) passing the Miraculin in a capture buffer through a capture column comprising a hydrophobic interaction chromatography medium of hydrophobicity sufficiently high to prevent the Miraculin from eluting in the presence of the equilibration buffer;
   (d) eluting the Miraculin from the capture column with an elution buffer as a purified fraction.

2. The method of claim 1, in which step (b) is performed without a chromatography column.

3. The method of claim 1, wherein preparing the miracle fruit extract comprises a step for mechanical depulping of the fruit.

4. The method of claim 1, further comprising ion exchange chromatography of the purified fraction of the Miraculin.

5. The method of claim 1, further comprising gel filtration of the purified fraction of the Miraculin.

6. The method of claim 1, further comprising ion exchange chromatography and gel filtration of the purified fraction of the Miraculin.

7. The method of claim 1, in which step (b) is carried out in a guard column connected in series to the capture column, and the capture buffer and equilibration buffer are equivalent.

8. The method of claim 7, in which the guard column contains butyl Sepharose and the capture column contains phenyl Sepharose.

9. The product of the process of claim 1.

10. The product of claim 9, wherein the Miraculin is at least 95% pure.

11. An alimentary product comprising the product of claim 9.

12. The product of claim 9, wherein the Miraculin comprises two variants, the major form having an additional amino-terminal aspartic acid residue.

13. A method for purifying Miraculin proteinaceous material comprising:
   (a) preparing a crude miracle fruit extract comprising Miraculin proteinaceous material and polyphenols;
   (b) passing the crude miracle fruit extract with an equilibration buffer solution through a guard column comprising a hydrophobic interaction chromatography medium of hydrophobicity sufficiently high to prevent the polyphenols from eluting from the column in the presence of the equilibration buffer solution, but sufficiently low that the proteinaceous material elutes as a fraction from the guard column with the equilibration buffer solution;
   (c) passing the proteinaceous fraction through a capture column coupled in series to the guard column, the capture column comprising a hydrophobic interaction chromatography medium of hydrophobicity sufficiently high to prevent the proteinaceous material from eluting in the presence of the equilibration buffer solution;
   (d) eluting the proteinaceous material from the capture column as a purified fraction in an elurion buffer.

14. The method of claim 13, further comprising the step of uncoupling the guard column and the capture column before eluting the proteinaceous material.

15. The method of claim 13, further comprising the step of regenerating the guard column by eluting the polyphenols with a regenerating reagent.

16. The method of claim 13, wherein the hydrophobic interaction chromatography media are selected from the group consisting of cross-linked agarose, cellulose, dextran, polyacrylamide, polystyrene crosslinked divinyl benzene, polymethacrylate, and combinations thereof.

17. The method of claim 13, wherein the low hydrophobicity hydrophobic interaction chromatography medium has covalently linked alkyl functional groups of $C_2$–$C_8$ and the high hydrophobicity hydrophobic interaction medium has covalently linked aromatic or heteroaromatic groups.

18. The method of claim 13, wherein the high hydrophobicity hydrophobic interaction medium is more highly substituted with alkyl ligands than the low hydrophobicity medium.

19. The method of claim 13, further comprising preconditioning the crude plant extract with a low-salt medium having a salt concentration equivalent to the equilibration buffer.

20. The method of claim 13, wherein the equilibration buffer includes a salt selected from the group consisting of ammonium sulfate, sodium sulfate, sodium citrate, sodium chloride, and potassium, magnesium, and calcium salts thereof, and combinations thereof.

21. The method of claim 13, wherein steps (b) to (d) are carried out at room temperature.

22. The method of claim 13, wherein the low hydrophobicity medium has butyl functional groups and the high hydrophobicity medium has phenyl functional groups.

23. The method of claim 13, wherein the low hydrophobicity medium has functional groups selected from the group consisting of isopropyl, octyl, and ether.

24. The product of the process of claim 13.

* * * * *